United States Patent [19]

Whitehead

[11] 4,430,990

[45] Feb. 14, 1984

[54] BODY HARNESS DEVICE

[76] Inventor: George Whitehead, 365 Hawthorne Cir., Apt. #4, Mt. Prospect, Ill. 60056

[21] Appl. No.: 382,394

[22] Filed: May 27, 1982

[51] Int. Cl.³ .............................................. A61B 19/00
[52] U.S. Cl. .................................... 128/1 R; 128/31; 128/134; 2/44
[58] Field of Search ................ 128/1 R, 31, 134; 2/44

[56] References Cited

U.S. PATENT DOCUMENTS

| 880,904 | 3/1908 | Mueller | 2/44 |
|---|---|---|---|
| 1,098,492 | 6/1914 | Gibson | 2/44 |
| 1,733,349 | 10/1929 | Koeber | 2/44 |
| 2,594,097 | 4/1952 | Twyman | 128/1 R |
| 3,191,599 | 6/1965 | Kendell | 128/134 |
| 4,343,299 | 8/1982 | Oxendine | 128/1 R |

Primary Examiner—Dalton L. Truluck
Attorney, Agent, or Firm—Welsh & Katz

[57] ABSTRACT

A body harness device is provided which finds particular application in the act of conjugal relations and which includes a pair of elongated straps each of which has a foot engagable stirrup thereon and terminates at an upper end in a shoulder strap arrangement such that in use the elongated straps are disposed generally lengthwise of the wearer and a force applied longitudinally downwardly on either of the elongated straps is distributed between both shoulders of the wearer while facilitating a desired relation between the marital partners.

8 Claims, 6 Drawing Figures

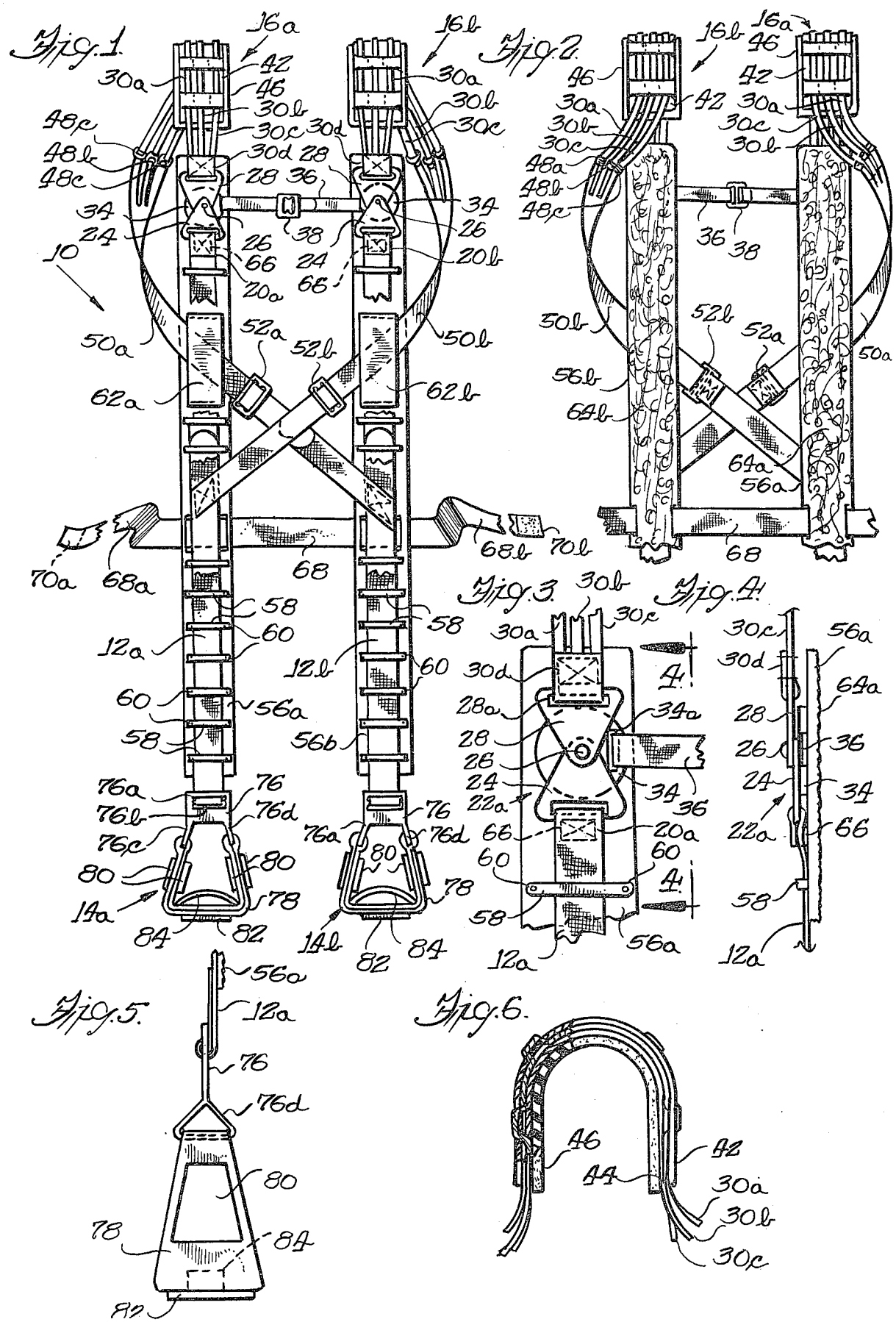

BODY HARNESS DEVICE

BACKGROUND OF THE INVENTION

The present invention relates generally to body harness devices, and more particularly to a body harness device for use during conjugal relations.

Devices have been proposed for use by human beings during conjugal relations wherein the device is worn by or acts on one of the marital partners and is responsive to manipulation or control by the other partner to establish a predetermined relation or movement between the partners. See, for example, U.S. Pat. Nos. 2,594,097 and 3,896,787. Such devices find particular application where one of the partners suffers a physical impairment or limitation which might otherwise inhibit conjugal relations. Significant disadvantages in the known devices of the type to which the present invention relates include the fact that the devices apply an uncomfortable breathing restraining restriction about the wearer's waist, as with the device disclosed in U.S. Pat. No. 2,594,097, or are rather bulky and awkward in structure so as to require substantial manipulation and positioning preparatory to use, as well as applying undesireable forces on the wearer's body, as in the case of the device disclosed in U.S. Pat. No. 3,896,787.

SUMMARY OF THE INVENTION

In accordance with the present invention, a body harness device is provided which finds particular use during conjugal relations and which employs a pair of substantially parallel laterally interconnected elongated straps each of which has a foot engagable stirrup thereon and terminates at its upper end in a shoulder strap arrangement adapted to engage the wearer's shoulders so that with the elongated straps disposed generally lengthwise of the wearer, a force applied longitudinally downwardly on either of the elongated straps is distributed between both shoulders of the wearer. Each shoulder strap arrangement includes a strap connected at one end to the corresponding elongated strap and adapted to extend forwardly over the wearer's shoulder and downwardly around the lateral rib area and diagonally across the back of the wearer to connect to the opposite elongated strap. Shoulder cushions or pads are cooperative with the shoulder encompassing strap portions so that the shoulder pads directly engage the wearer's shoulders in contoured relation therewith, and a waist strap traverse to the elongated straps is adapted to extend about the wearer's waist to assist in maintaining the elongated straps in relatively stable spaced relation.

One feature of the body harness device in accordance with the present invention lies in the provision of elongated pads in the form of leather backing members mounted on the elongated straps and having soft exposed surfaces adapted to engage the wearer's back.

Another feature of the body harness device in accordance with the present invention lies in the provision of elongated straps which are adjustable in length to enable selective positioning of the stirrups, and the provision of shoulder straps which are interconnected to the corresponding elongated straps through swivel connections which allow the shoulder straps to more readily conform to the contour of the wearer's shoulders.

Further objects, features and advantages of the invention will become apparent from the following detailed description of the invention when taken in conjunction with the accompanying drawing wherein like reference numerals designate like elements throughout the several views.

BRIEF DESCRIPTION OF THE DRAWING

FIG. 1 is a rear elevational view of a body harness device constructed in accordance with the present invention;

FIG. 2 is a fragmentary front elevational view of the body harness device of FIG. 1;

FIG. 3 is a fragmentary elevational view, on an enlarged scale, illustrating one of the swivel connections between the elongated straps and the associated shoulder engaging strap portions;

FIG. 4 is a fragmentary side elevational view taken substantially along line 4—4 of FIG. 3, looking in the direction of the arrows;

FIG. 5 is a fragmentary side elevational view of one of the stirrups employed in the harness device of FIG. 1; and FIG. 6 is a fragmentary side view of a shoulder engaging strap and associated cushion pad employed in the harness device of FIG. 1.

DESCRIPTION OF PREFERRED EMBODIMENT

Referring now to the drawing and in particular to FIG. 1, a body harness device constructed in accordance with the present invention is indicated generally at 10. The body harness device 10 is adapted to be worn by a human being and finds particular utilization during conjugal relations between marital partners. Very generally, the body harness device 10 includes a pair of substantially identical elongated straps, indicated generally at 12a and 12b, respectively, each of which has foot engagable means mounted thereon in the form of a stirrup, indicated generally at 14a and 14b, respectively, and terminates at its upper end in a shoulder strap arrangement, indicated generally at 16a and 16b, respectively, adapted to engage the wearer's shoulders so that when the harness device is fitted onto a wearer with the elongated straps disposed generally lengthwise of the wearer, a force applied substantially longitudinally downwardly on either of the elongated straps 12a, 12b is distributed in an isodynamic fashion between both shoulders of the wearer.

The elongated straps 12a,b are preferably made of a woven high strength fabric material such as nylon so as to form a high strength flexible relatively thin fabric strap. Each elongated strap 12a,b is connected at an upper end 20a,b, respectively, to swivel connection means, indicated generally at 22a and 22b, respectively, which serve to interconnect the elongated straps to the respective shoulder strap arrangements 16a,b. As illustrated in FIGS. 3 and 4, each of the swivel connection means 22a,b includes a first generally triangular connector plate 24 made of a suitable metallic or plastic material and having an elongated opening 24a formed therethrough to receive the upper end of the associated elongated strap 12a or 12b which is looped and sewn to establish a fixed connection to the corresponding connector plate 24. Each connector plate 24 is pivotally connected through a connector pin 26 to a second similar triangular connector plate 28 having an elongated opening 28a therethrough to facilitate connection to flexible fabric shoulder straps in the form of three generally parallel relatively narrow straps 30a, 30b and 30c each set of which forms a portion of the corresponding shoulder strap arrangement 16a or 16b. The straps 30a,b and c may be fewer or greater in number than three and are affixed to the associated triangular connector plates 28 as by sewing to connector straps 30d in similar fashion to connection of straps 12a,b to their associated connector plates 24.

A generally circular swivel plate 34 is pivotally mounted on each of the connector pins 26 rearwardly of the connector plates 26 and 28, as viewed in FIGS. 1 and 3, and has an elongated opening 34a therethrough which is adpated to slidingly receive a transverse upper cross strap 36 therethrough. The strap 36 has a buckle 38 secured to one end to facilitate connection to the opposite end and thereby enable selective adjustment of the lateral spacing between the upper ends of elongated straps 12a,b.

The shoulder straps of each set of straps 30a, 30b, and 30c extend through a plurality of aligned loops formed in a corresponding rectangular shoulder piece 42 which preferably is made from leather to facilitate forming the aligned loops by transverse slits formed in the rectangular shoulder pieces. Referring to FIG. 6, taken in conjunction with FIGS. 1 and 2, each of the rectangular shoulder pieces 42 is secured to an underlying similar size leather base piece 44, as by sewing about their peripheral edges, so as to assume a generally inverted U-shaped configuration. A cushion pad 46 made from a suitable sponge-like material is adapted to be releasibly secured to the exposed surface of each of the base pieces 44 as through Velcro type attaching means. The cushion pads 46 have lateral or transverse widths slightly greater than the transverse widths of the corresponding shoulder pieces 42,44 and each has a length, considered along its arcuate profile, sufficient to comfortably engage the corresponding shoulder of the wearer. Releasable connection of the cushion pads 46 to the base pieces 44 enables removal of the cushion pads for periodic cleaning.

Each of the straps 30a,b and c has a free end, opposite its connection to the associated connector strap 30d, which is adjustably connected through a suitable buckle connector 48a, 48b, and 48c, respectively, to a corresponding strap 50a or 50b which also forms a part of the corresponding shoulder strap arrangement 16a,b. The shoulder straps 30a,b and c and associated straps 50a,b are adapted to extend forwardly over the wearer's shoulders from the elongated straps 12a,b which extend lengthwise of the wearer's back, whereafter straps 50a,b extend downwardly and laterally outwardly around the corresponding lateral rib area of the wearer from which the straps 50a,b extend diagonally across the back of the wearer. Preferably each of the straps 50a,b comprises a two piece strap with the two pieces being interconnected by a buckle, as indicated at 52a,b respectively, to facilitate variable length adjustment. The lower strap portion of each two-piece strap 50 is connected to the opposite elongated strap 12a,b as by being sewn thereto, as illustrated in FIG. 1. The buckles 48a,b and c are positioned to lie along the lateral rib areas of the wearer and facilitate strap length adjustment to accommodate different size users.

In accordance with one feature of the body harness device 10, each of the elongated straps 12a and 12b has an elongated backing member, indicated at 56a and 56b respectively, operatively associated therewith for engagement with the skin of the user. The backing members 56a,b have transverse widths greater than the associated straps 12a and 12b and are adapted to be supported by the elongated straps so as to extend from an upper position overlying the swivel connection means 22a,b, as viewed from the front of the harness device in FIG. 2, downwardly to a position spaced below the waist area of the user. The backing members 56a and 56b are preferably made of flexible leather or the like and have a plurality of transverse cross pieces 58, which also may be of leather, affixed thereto as through rivets 60 or other suitable attaching means so as to define loops along the length of the backing members to facilitate sliding retention of the associated straps 12a,b in side-to-side relation. Rectangular leather pieces 62a and 62b are affixed, respectively, to the backing members 56a,b as by transverse stitching so as to define transverse loops through which the diagonally disposed straps 50a,b extend.

Each of the elongated backing pieces 56a and 56b has a soft exposed surface thereon, indicated at 64a and 64b, respectively, opposite the side on which the cross pieces 58 are secured. The soft exposed surfaces 64a,b may be formed by a fleece coating or woven fabric backing secured on the leather backing pieces 56a,b, and provide soft surfaces for contact with the wearer's body so as not to irritate the skin. Preferably, means in the form of Velcro type fasteners, indicated at 66 in FIGS. 1, 3 and 4, are secured to the mutually facing surfaces of the upper strap ends 20a,b and the associated backing members 56a,b so as to releasibly maintain the backing members in fixed relation along the elongated straps 12a,b.

A waist strap or band 68 extends between the elongated straps 12a,b in transverse relation thereto and has free end portions 68a and 68b of sufficient length to enable the waist strap to releasibly encircle the wearer's waist in loose fitting relation. The waist strap 68 preferably has an elastic center portion with woven fabric end portions 68a,b and extends through suitable pairs of elongated openings in the backing members 56a,b so as to enable selective lateral spacing of the backing members and associated elongated straps 12a,b along the length of the waist strap. The free ends of the waist strap are adapted to be releasibly secured to each other when encircling the wearer's waist as, for example, by mating Velcro fastener means 70a,b formed on the opposite terminal ends of the waist strap. It is envisioned that the waist strap 68 might be suecred comfortably about the users waist but released during conjugal relations.

The elongated straps 12a,b are made of sufficient length to extend downwardly from the connector plates 24 through the loops or transverse cross pieces 58 on the backing members 56a,b, respectively, and allow the free ends of the elongated straps to be looped back upon themselves and again passed upwardly through the loops 58. In this manner, each strap 12a,b defines a loop end opposite its connection to the assoicated shoulder strap arrangement 16a,b. The loop ends provide means for mounting the stirrups 14a,b on the elongated straps in a manner to enable the positions of the stirrups to be selectively varied relative to corresponding shoulder strap arrangements. In the condition of the harness device illustrated in FIG. 1, the free ends of straps 12a,b opposite the connector plates 24 are looped back upon themselves beneath the cross pieces 58 such that the stirrups 14a,b are located at what would be approximately the knee length of the wearer. In use, however, the straps 12a,b are extended to position the stirrups 14a,b to a desired distance below the waist strap 68.

Referring to FIG. 5, taken in conjunction with FIG. 1, each of the stirrups 14a,b includes a connecting bracket 76 which may be made of a suitable strength plastic or metallic material and which has a pair of transverse parallel slots or openings 76a and 76b formed therethrough which enable the corresponding elongated strap 12a or 12b to be slidably adjustably inserted through the slots 76a,b in a generally coupled loop fashion, as is known. Each of the brackets 76 has a pair of spaced generally triangular open centered support hoops 76c and 76d formed thereon which facilitate mounting of a woven fabric strap 78 to each bracket so as to form a foot engageable stirrup. The stirrup straps 78 are preferably of double thickness and are generally trapezoidal in side contour, as illustrated in FIG. 5. The stirrup straps have pairs of leather reinforcing pieces 80 and 82 affixed thereto as by sewing to provide reinforcement and maintain the fabric stirrups in a desired open loop configuration as illustrated in FIG. 1. Preferably, an elastic retaining strap 84 is affixed within each of the stirrups 14a,b to be received over a foot when inserted within the stirrup.

Thus, in accordance with the present invention, a body harness device is provided to be worn by a human being which includes substantially parallel laterally spaced elongated straps 12a,b each of which has an upper end terminating in a shoulder strap arrangement 16a,b adapted to engage the wearer's shoulders with the elongated straps disposed generally lengthwise along the back of the wearer so that the soft exposed surfaces 64a,b of the backing members 56a,b engage the wearer's skin. Foot engageable means in the form of the stirrups 14a,b are connected to each of the elongated straps 12a,b and are adjustable in position relative to the shoulder engaging strap portions 16a,b so as to optimize comfort to the users. When worn, the shoudler strap portions 16a,b, by virtue of the diagonally disposed straps 50a,b, serve to distribute between both shoulders of the wearer any forces applied generally longitudinally downwardly on either of the elongated straps, while the swivel connections 22a,b enable the shoulder strap portions and associated cushion pads to more readily conform to the contour of the wearer's shoulders. Each of the diagonal straps 50a,b also cooperates with its associated set of shoulder straps 30a,b and c to effect a rearward pull on the corresponding shoulder area of the wearer and initiate a forward thrust of the wearer's midsection when a force is applied longitudinally downwardly on the corresponding elongated strap 12a or 12b. A desired result of the body harness device is that the leg muscles of the partner whose feet are inserted into the stirrups share the work load of the abdominal muscles without obstructing breathing.

While a preferred embodiment of the invention has been illustrated and described, it will be understood that changes and modifications may be made therein without departing from the invention in its broader aspects. Various features of the invention are defined in the following claims.

What is claimed is:

1. A body harness device for use by male and female partners during coitus and adapted to be worn by one of the partners, said device comprising a pair of elongated straps each of which has an end terminating in a shoulder strap arrangement adapted to engage the wearer's shoulders with the elongated straps disposed generally lengthwise of the wearer's back in substantially parallel laterally spaced relation along their full lengths, a waist strap cooperative with and extending transverse to said laterally spaced elongated straps, said waist strap being adapted to releasably encircle the wearer's waist, each of said shoulder strap arrangements including a shoulder strap pivotally connected to the terminal end of the corresponding elongated strap and configured to extend forwardly from the back of the wearer over a corresponding shoulder of the wearer and thereafter extend downwardly and rearwardly about the corresponding lateral rib area and diagonally across the wearer's back to connect to the opposite elongated strap such that a force applied generally longitudinally downwardly on either one of the elongated straps when extending lengthwise of the wearer effects application of a force on each of the wearer's shoulders which is of less magnitude than the applied force, and foot engageable means connected to each of said elongated straps at a position spaced from the corresponding shoulder strap arrangement so as to enable selective application of downward forces on said elongated straps.

2. A body harness device as defined in claim 1 wherein said foot engagable means comprises a stirrup connected to each of said elongated straps at a position thereon spaced from the corresponding shoulder strap arrangement.

3. The body harness device as defined in claim 2 including an elastic retaining strap associated with each of said stirrups for retaining a foot inserted within the corresponding stirrup.

4. A body harness device as defined in claim 1 wherein each of said shoulder strap arrangements includes a contoured cushion pad adapted to directly engage the corresponding shoulder of the wearer.

5. A body harness device as defined in claim 1 wherein said elongated straps are adapted for variable length adjustment.

6. A body harness device as defined in claim 1 including an elongated backing member operatively associated with each of said elongated straps, each of said backing members having a plurality of transverse loops thereon adapted to receive the corresponding elongated strap in sliding relation therethrough, each of said backing members having a generally planar exposed surface establishing a soft surface adapted to engage the wearer's back.

7. A body harness device as defined in claim 6 wherein each of said elongated straps is of sufficient length to enable it to be looped back upon itself so as to define a loop end opposite its connection to the associated shoulder strap arrangement, said foot engagable means comprising a pair of stirrups each of which is adapted to be mounted on an associated one of said elongated straps at said loop end thereon and being selectively positionable to accommodate variable adjustment of the spatial relation of each stirrup from the corresponding shoulder strap arrangement.

* * * * *